US012629437B2

(12) United States Patent
Liu et al.

(10) Patent No.: US 12,629,437 B2
(45) Date of Patent: May 19, 2026

(54) MEDICAL INSTRUMENT DISINFECTING ENCLOSURE

(71) Applicant: LUMICARE IP PTY LTD, Victoria (AU)

(72) Inventors: Tong Liu, Victoria (AU); Andrew Kobylinski, Victoria (AU); Matthew Hollier, Victoria (AU); Bo Sun, Victoria (AU); Guang Gao, Victoria (AU)

(73) Assignee: LUMICARE IP PTY LTD, Victoria (AU)

( * ) Notice: Subject to any disclaimer, the term of this patent is extended or adjusted under 35 U.S.C. 154(b) by 897 days.

(21) Appl. No.: 17/614,908

(22) PCT Filed: May 31, 2020

(86) PCT No.: PCT/AU2020/000044
§ 371 (c)(1),
(2) Date: Nov. 29, 2021

(87) PCT Pub. No.: WO2020/237282
PCT Pub. Date: Dec. 3, 2020

(65) Prior Publication Data
US 2022/0160914 A1     May 26, 2022

(30) Foreign Application Priority Data
May 31, 2019    (AU) ................................. 2019901886

(51) Int. Cl.
A61L 2/10      (2026.01)
A61B 90/70     (2016.01)
A61L 103/15    (2026.01)
(52) U.S. Cl.
CPC ................ A61L 2/10 (2013.01); A61B 90/70 (2016.02); A61L 2103/15 (2026.01);
(Continued)

(58) Field of Classification Search
CPC .. A61L 2/10; A61L 2202/11; A61L 2202/121; A61L 2202/122; A61L 2202/24; A61B 90/70
See application file for complete search history.

(56) References Cited

U.S. PATENT DOCUMENTS

2008/0265179 A1* 10/2008 Havens ...................... A61L 2/10
                                                        250/492.1
2009/0171163 A1    7/2009 Mates et al.
(Continued)

FOREIGN PATENT DOCUMENTS

CN          107854704 A       3/2018
CN          108969782 A      12/2018
WO       2020237282 A1      12/2020

OTHER PUBLICATIONS

International Search Report and Written Opinion of the International Searching Authority for related International Patent Application No. PCT/AU2020/000044, dated Aug. 11, 2020, 13 pages.

*Primary Examiner* — Timothy C Cleveland
(74) *Attorney, Agent, or Firm* — DITTHAVONG, STEINER & MLOTKOWSKI

(57) ABSTRACT

There is disclosed a disinfecting enclosure for a medical instrument comprising: a plurality of modules configured to define an enclosure having a base and at least one upright wall extending from the base; and a lid member configured to be mounted on the at least one upright wall so as to enclose the enclosure; wherein each said module comprises an inner surface having a plurality of UVC LEDs provided thereon, each of the plurality of UVC LEDs being actuable to emit UVC light to irradiate all surfaces of a medical instrument located within the enclosure.

16 Claims, 14 Drawing Sheets

(52) U.S. Cl.
CPC ...... *A61L 2202/11* (2013.01); *A61L 2202/121*
(2013.01); *A61L 2202/122* (2013.01)

(56)                    References Cited

U.S. PATENT DOCUMENTS

| | | | |
|---|---|---|---|
| 2014/0217307 | A1 | 8/2014 | Messina et al. |
| 2014/0341777 | A1 | 11/2014 | Deshays et al. |
| 2016/0114066 | A1 | 4/2016 | Lichtblau |
| 2016/0324996 | A1 | 11/2016 | Bilenko et al. |
| 2017/0100495 | A1* | 4/2017 | Shur ...................... H04N 7/183 |

* cited by examiner

Transducer head position in the enclosure. The upper limit

Transducer head position in the enclosure. The lower limit

Scale indicator for position the transducer's head in optimal position

10

30

34

MEDICAL INSTRUMENT DISINFECTING ENCLOSURE

RELATED APPLICATIONS

The present application claims priority from Australian Provisional Patent Application No. 2019901886, filed 31 May 2019, the entire contents of which are incorporated herein by reference

FIELD OF INVENTION

The present invention relates generally to a disinfecting device for medical instruments, and in particular, to a disinfecting enclosure that employs Ultraviolet Type C (UVC) light irradiation to eliminating the presence of microorganisms on the surface of medical instruments, such as ultrasound transducers.

BACKGROUND OF THE INVENTION

Within the medical industry, a variety of different types of sterilisation and disinfecting systems have been proposed for use on a variety of different devices and equipment. The degree of sterilisation or disinfection required for a specific device or piece of equipment will largely depend upon the manner in which the device or equipment is used and the likelihood of cross-contamination between users of the device or equipment.

In the field of diagnostic ultrasound machines, ultrasound transducers are employed which are used to contact the human body in order to generate appropriate images for analysis by healthcare professionals. Such transducers are used in a variety of different applications depending upon the area of the body requiring imaging. In this regard, the transducers may be used in contact with individuals having healthy and intact skin, through to individuals with skin lacerations and other conditions where the transducer may be in direct contact with mucous membranes and blood and other bodily secretions. Due to the large range of use of such transducers on individuals with a variety of different conditions, there is an increased likelihood that the surface of the transducer may be in contact with various microorganisms which are carried on the surface of the transducer. Thus, it is critically important that after use, such transducers undergo a high level disinfecting or sterilisation process, to eliminate any organisms that may be present on the surface thereof.

To achieve such a high-level degree of disinfection, there exist currently four processes capable of fulfilling this requirement. These processes include: chemical soaking, chemical aerosol, surface wiping, and UVC irradiation:

Chemical soaking is a process that requires placing the ultrasound transducer such that it is immersed into a chemical reagent. One example of such system is the GUS Disinfection Soak Station made by CIVCO Medical Solutions. Such processes generally require a soaking time for the transducer to be left immersed in the chemical reagent of between around 8 minutes to 45 minutes. Whilst the appropriate level of disinfection may be achievable, the disadvantage of this process is that the chemical reagent is hazardous and any exposure to the chemical reagent may harm the operator and patient and disposal of the chemical waste may harm the environment. Further, as care is required in handling the chemicals, this method is manually operated and time-consuming.

Chemical aerosol is a process whereby the ultrasound transducer is placed within a chamber that is flooded with a nebulised hydrogen peroxide. One example of such a commercially available system that employs this process is the system developed by Nanosonics Ltd., under the brand Trophon. Typically, the transducer is placed within the chamber for between 7 to 12 minutes, depending on the specific conditions. Once again, due to the use of the chemical reagent, the disadvantage of this method is that the residual of chemical reagent left on transducers may harm the operators and patients.

It is possible to achieve the desired level of disinfection through the use of surface wipes. Such a process uses different chemical wipe combinations to manually wipe the surface of the transducer. The procedure requires steps of pre-cleaning, disinfection and rinsing. One example of such a commercially available method of using surface wipes is using chlorine dioxide formulation made by Tristel. However, a drawback with such a method is that it requires manual application and is prone to human error, costly and is time intensive.

The remaining process for achieving such a high-level degree of disinfection is through the use of UVC irradiation, typically by way of lighting through mercury vapour tubes. Such a process requires the ultrasound transducer to be positioned within a chamber having multiple mercury vapor tubes as light sources for disinfection. There are several commercial systems available which utilise UVC irradiation to disinfect ultrasound transducers. However, all of these systems use mercury vapour tubes as their UVC light source. Such tubes pose a potential risk to operators who may be exposed to mercury vapour leakage from the tubes. In addition, the disposal of these mercury vapour tubes is harmful to the environment and requires additional cost and complexity to do so in a safe way. Such disposal problems are significant and have been raised by the UN Minamata Convention on Mercury in 2013, where an international treaty was enacted to protect human health and the environment from anthropogenic emissions and releases of mercury and mercury compounds. This treaty sets down controlling measures over a variety of products containing mercury, the manufacture, import and export of which will be altogether prohibited by 2020.

In addition to the problems associated with continuing to use mercury vapour tubes, such tubes can only emit UVC with wavelength at 254 nm, which is inefficient for germicidal efficacy, requiring longer exposure times to achieve the desired level of disinfection.

Thus, there is a need to provide an alternative process for achieving high-level disinfection of ultrasound transducers and the like, that is highly-efficient, safe and environmentally friendly.

The above references to and descriptions of prior proposals or products are not intended to be, and are not to be construed as, statements or admissions of common general knowledge in the art. In particular, the above prior art discussion does not relate to what is commonly or well known by the person skilled in the art, but assists in the understanding of the inventive step of the present invention of which the identification of pertinent prior art proposals is but one part.

STATEMENT OF INVENTION

The invention according to one or more aspects is as defined in the independent claims. Some optional and/or preferred features of the invention are defined in the dependent claims.

Accordingly, in one aspect of the invention there is provided a disinfecting enclosure for a medical instrument comprising: a plurality of modules configured to define an enclosure having a base and at least one upright wall extending from the base; and a lid member configured to be mounted on the at least one upright wall so as to enclose the enclosure; wherein each said module comprises an inner surface having a plurality of UVC LEDs provided thereon, each of the plurality of UVC LEDs being actuable to emit UVC light to irradiate all surfaces of a medical instrument located within the enclosure.

In one aspect of the invention, each module further comprises a heat dissipation member for dissipating heat generated by the UVC LEDs away from the inner surface thereof.

The plurality of modules may comprise a plurality of side wall modules for forming the at least one upright wall of the enclosure and at least one base module for forming the base of the enclosure.

In one embodiment, a frame member may be provided for configuring the modules, the frame member may have a plurality of open spaces into which the plurality of modules may be inserted to form the enclosure. The enclosure may be in the form of a polyhedron and the modules may form a base and sidewalls of the polyhedron. The polyhedron may be an octagonal polyhedron.

In another embodiment, the modules may be directly configured together, without a frame member. In this embodiment, the modules are assembled to form the enclosure in the desired shape, including the base and sidewalls of enclosure.

In one embodiment, the distance between adjacent UVC LEDs on the inner surface of the base module (denoted as "L") may be less than:

$$2D * \tan\frac{\phi}{2} \text{ or } 15 \text{ cm};$$

where, D is the distance between the UVC LEDs and the medical instrument and $\phi$ is an illumination angle of the UVC LEDs.

In another embodiment, the distance between adjacent UVC LEDs on the inner surface of the side wall module (denoted as "L") is less than:

$$2D * \tan\frac{\phi}{2} \text{ or } 15 \text{ cm};$$

where D is the distance between the UVC LEDs and the medical instrument and $\phi$ is an illumination angle of the UVC LEDs.

The heat dissipation member may comprise a heat sink mounted on an external surface of each of the modules that conducts heat from the UVC LEDs away from the enclosure.

The distance between the UVC LEDs and the closest surface of medical instrument may be greater than 1 cm and less than 20 cm.

The lid member may comprise a suspension mechanism or clamping mechanism for hanging or holding the medical instrument inside of the enclosure.

The medical instrument may be an ultrasound transducer.

In another aspect, there is provided a disinfecting chamber comprising a plurality of chamber walls configured to form an enclosed space, each chamber wall having a plurality of windows formed therein, each window being configured to be transparent to UVC light so as to allow the UVC light to transmit therethrough, one or more UVC LED chips are mounted onto a light board that is attached to an outer side of the chamber walls such that the one or more UVC LED chips mounted thereto are positioned adjacent a window to transmit the UVC light through the window and into the enclosed space, wherein one or more heat sinks are mounted to a rear surface the light board for transmitting and dissipating heat transmission generated by the one or more UVC LED chips.

BRIEF DESCRIPTION OF THE DRAWINGS

The invention may be better understood from the following non-limiting description of preferred embodiments, in which.

DETAILED DESCRIPTION OF THE DRAWINGS

Preferred features of the present invention will now be described with particular reference to the accompanying drawings. However, it is to be understood that the features illustrated in and described with reference to the drawings are not to be construed as limiting on the scope of the invention.

The present invention will be described below in relation to its application for use in disinfecting a transducer for a medical ultrasound device. However, it will be appreciated that the present invention could be used in a variety of different applications, both medical and non-medical, where disinfection of an element is required.

Figure 1:
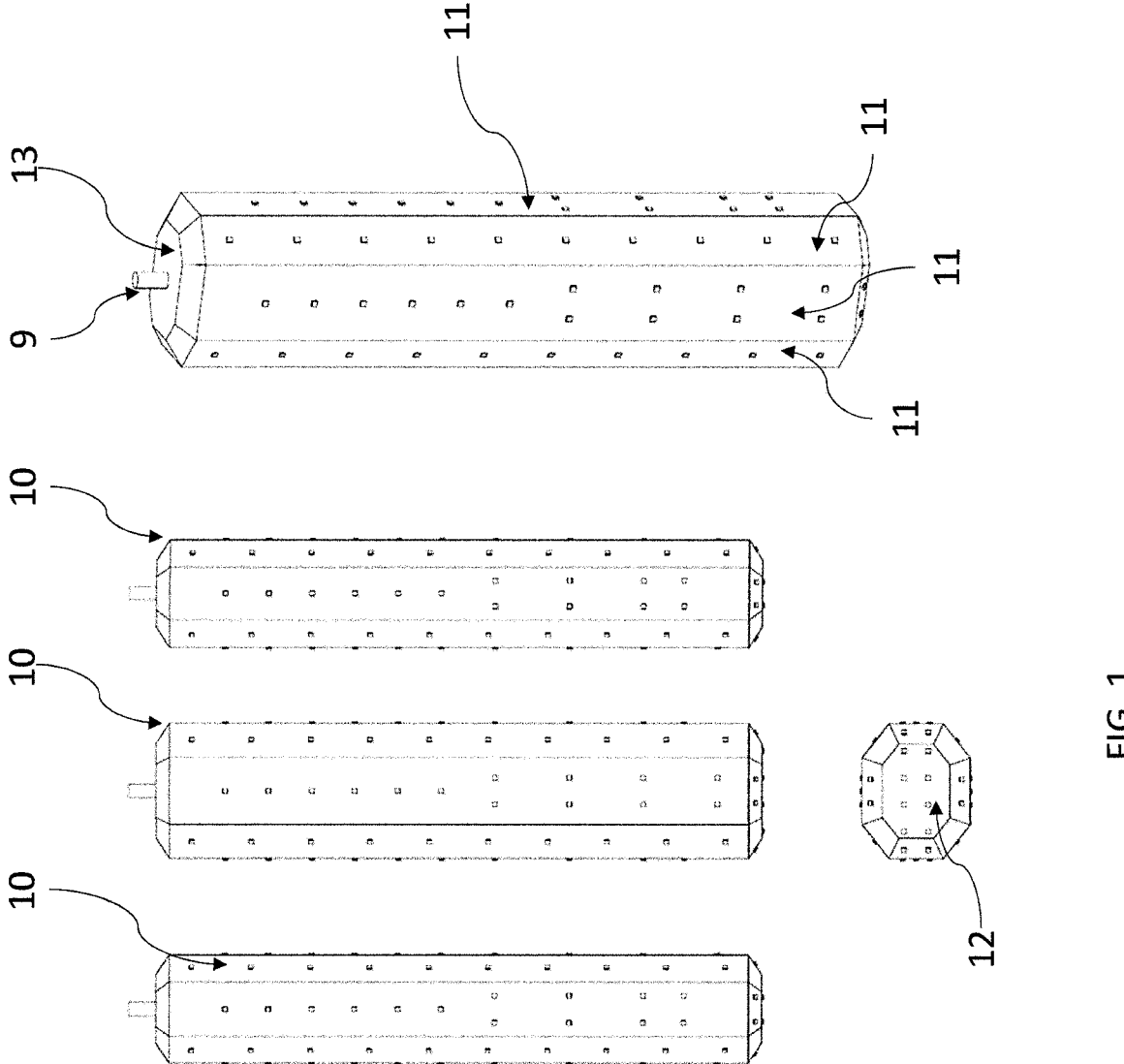
FIG. 1 is a schematic layout depicting an embodiment of UVC LEDs suitable for use with the disinfecting device of the present invention.

Referring initially to FIG. 1, there is depicted an isolated UVC disinfecting enclosure 10, made up of a plurality of modules 11, in accordance with a preferred embodiment of the present invention. The modules 11 are arranged to form an enclosure, into which a transducer device is to be placed for disinfecting the surface thereof, as will be discussed in further detail below.

The enclosure 10 is depicted as having a multi-sided (for example, octagonal) polyhedron shape with each of the modules 11 being configured to abut an adjacent module 11 to define an enclosed space that forms the enclosure 10. In this regard, a base module 12 and a lid member 13 are provided to fully enclose the space or enclosure and the modules support UVC LEDs such that the internal surfaces of the modules 11 and 12 have UVC LEDs formed thereon to emit UVC light to irradiate all surfaces of an ultrasound transducer that is suspended within the enclosure 10.

Figure 2:
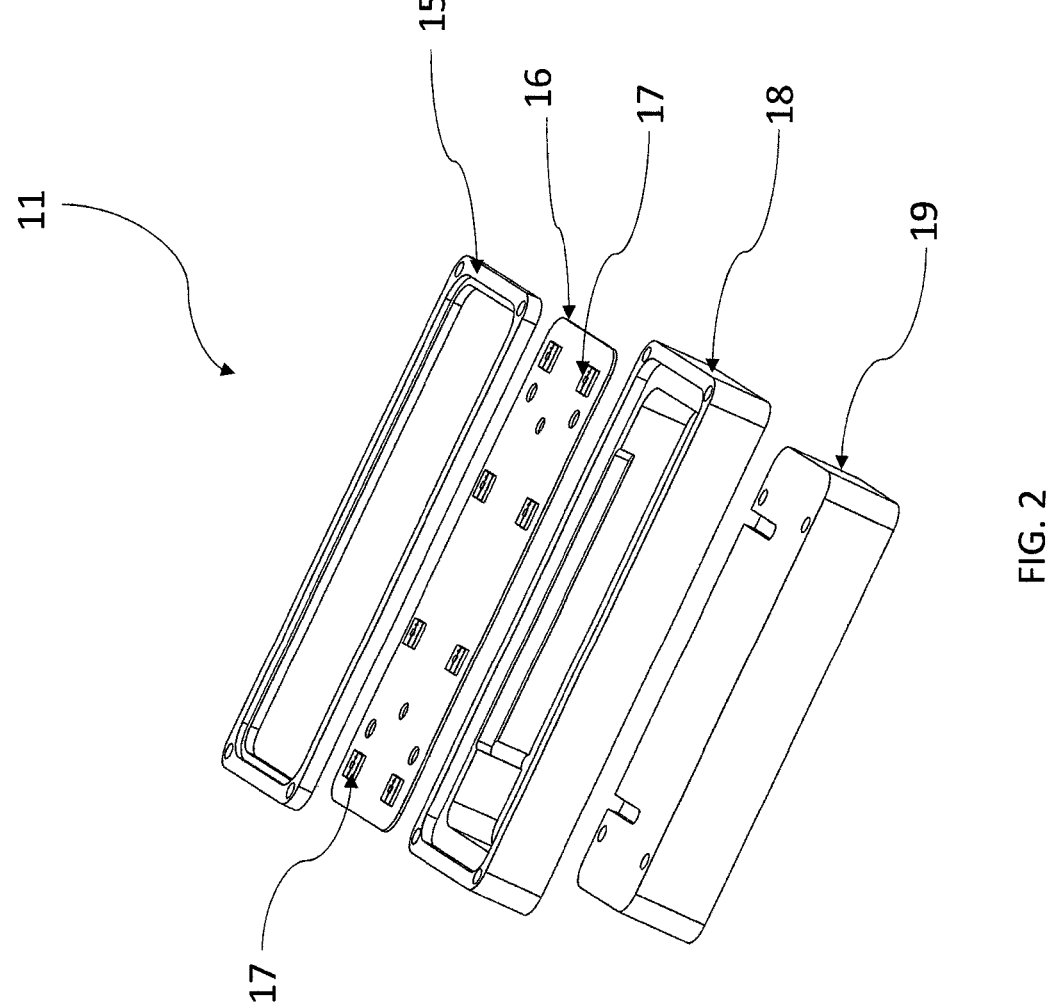
FIG. 2 is a schematic diagram of an exploded view of a light source for use with the UVC disinfecting device in accordance with an embodiment of the present invention.

Referring to FIG. 2, a schematic diagram of an exploded view of an embodiment of a light source module 11 is depicted. The light source module comprises a cover member 15 which is configured to engage with a frame member 18 by way of one or more screws, or buckles, or the like. A UVC LEDs board 16 is mounted between the cover member 15 and the heat sink 19. The light board 16 comprises a plurality of UVC LED 17 positioned over the surface thereof for delivering the light into the internal space of the enclosure 10. The heatsink 19 faces away from the enclosure 10 and is in contact with the light board 16 to dissipate heat generated by the UVC LED 17 away from the enclosure 10. In the embodiment as depicted in FIG. 2, a frame member 18 is employed to hold the light board 16 and the heat sink 19 together, although such a frame member is optional.

Figure 3:
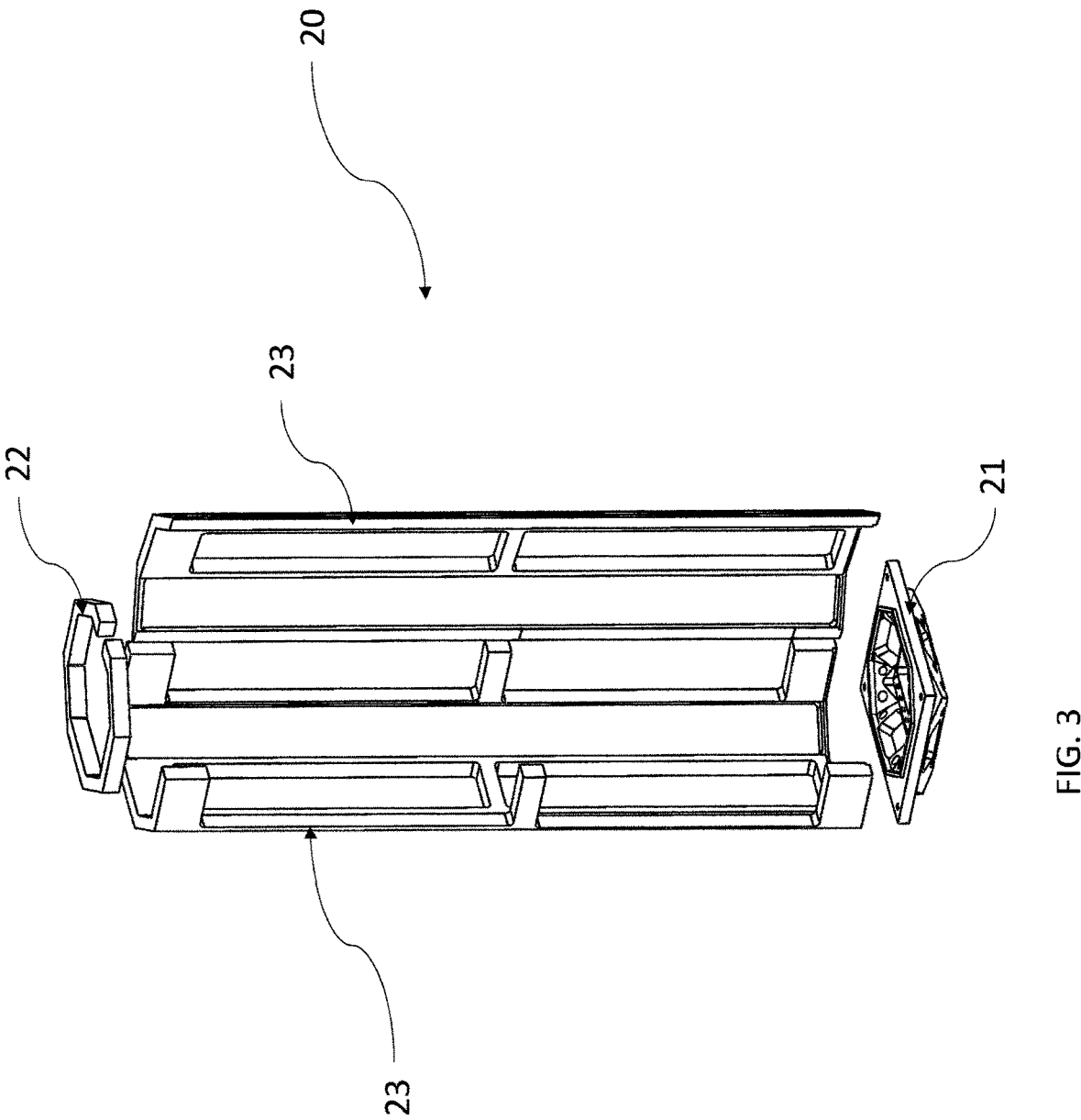
FIG. 3 is an exploded view showing the structural make-up of the disinfection enclosure frame of a UVC disinfecting device in accordance with an embodiment of the present invention.

Whilst the modules 11 and 12 are of a different shape and size to each other, the base module 12 is constructed in the manner shown in FIG. 2. Once the modules have been assembled, the modules 11, 12 and the lid member 13 (which could comprise no UVC LEDs) are mounted within a disinfecting enclosure frame construction 20 as depicted in FIG. 3.

Figure 4:
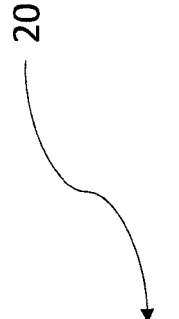
FIG. 4 is a schematic view depicting the assembled structure of the disinfection enclosure frame of a UVC disinfecting device in accordance with an embodiment of the present invention.
Figure 4:
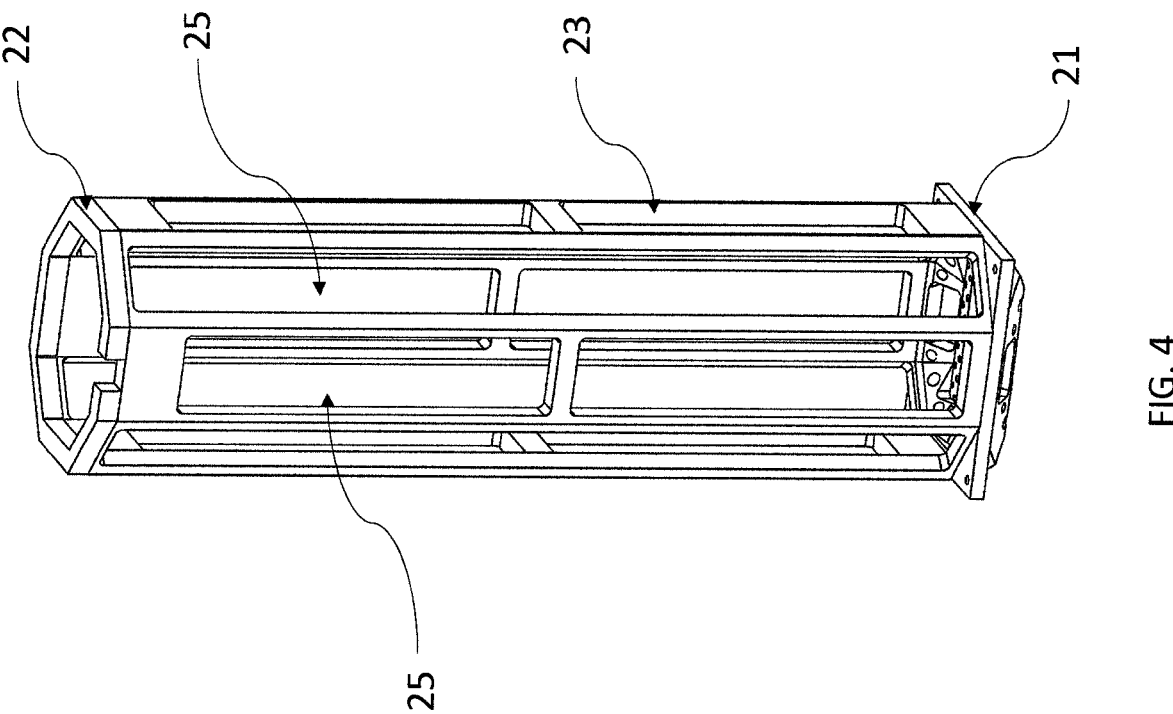

The disinfecting enclosure frame construction 20 comprises a base member 21, a top member 22 and a plurality of side members 23 which are assembled together to form the assembled disinfecting enclosure frame 20, as depicted in FIG. 4. Due to the octagonal polyhedron shape of the frame 20, in a preferred embodiment, there are four side members 23, each consisting of two upright wall sections angled with respect to each other, as depicted in FIG. 3. Three of the side wall members 23 are fixed in position with respect the base member 21 and top member 22, with the fourth side wall member 23 being hingedly mounted to a neighbouring side wall member along one connecting edge, to form a door for opening and accessing the enclosure of the assembled disinfecting enclosure device.

Figure 5:
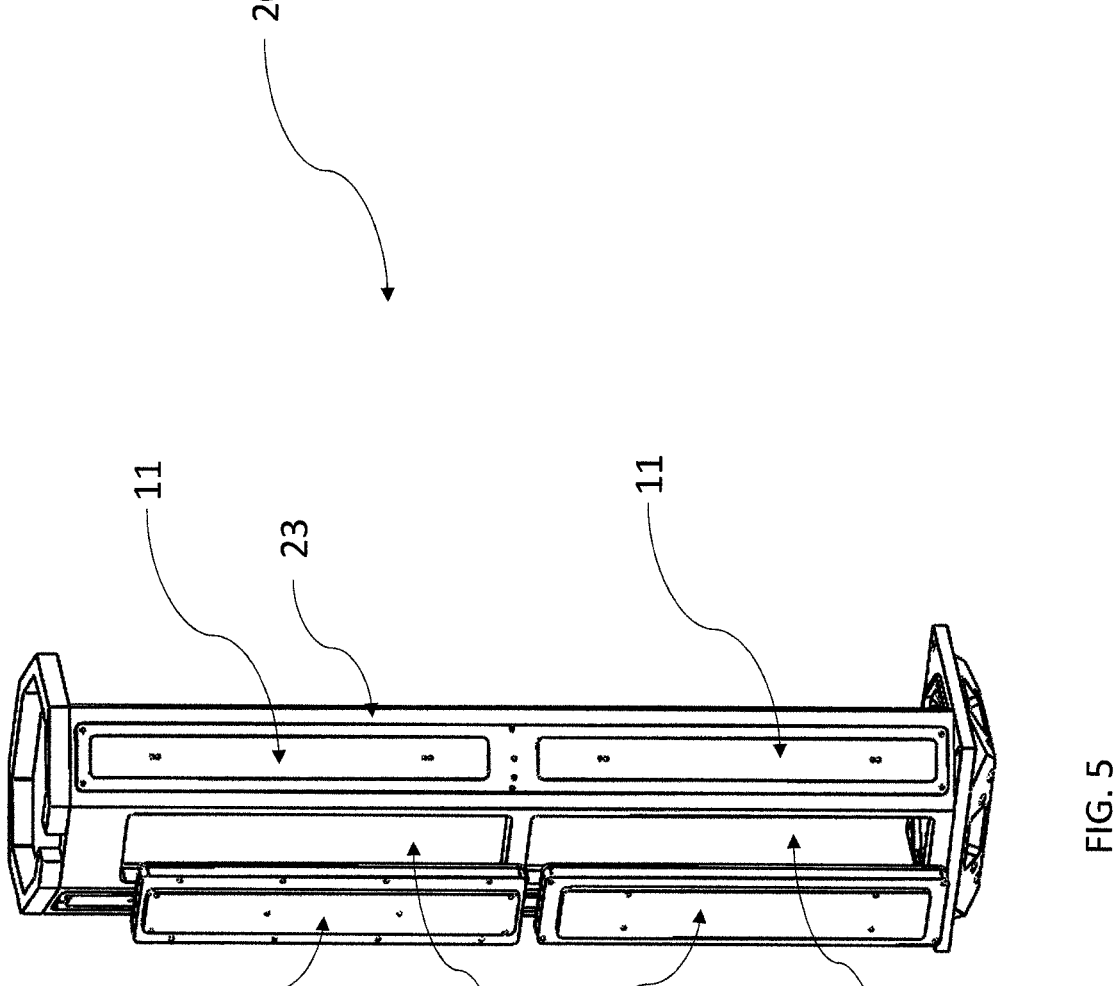
FIG. 5 is a schematic view depicting a partially assembled structure of the UVC disinfecting device in accordance with an embodiment of the present invention.

Referring to FIG. 5, the manner in which the light source modules 11 are mounted within the side members 23 of the disinfecting enclosure frame 20 is shown. In a preferred embodiment, the light source modules 11 are secured in position within the pre-formed recesses 25 formed in the side members 23 by way of mechanical fastening means, such as screws, rivets and the like. As will be appreciated, the base module 12 and lid member 13 will also be mounted within the pre-formed recess formed in the base member 21 and top member 22 respectively.

Once the light source modules 11, 12 and 13 have been fully assembled within the frame 20, the resultant disinfecting enclosure will have the UVC LEDs evenly distributed around the surfaces of the resultant enclosure or space. As desired, the modules 11 and 12 can be simply and effectively detached from the frame 20 and replaced as required.

In a preferred embodiment, for each of the modules 11 and 12, the chips of the UVC LED 17 are directly mounted on the light board 16 which is on contact with the heatsink 19 to facilitate heat dissipation from the UVC LED 17. This arrangement enables the irradiation intensity in the unit area of the disinfecting enclosure to be increased to a level as desired.

Referring again to FIG. 1, the layout of the modules 11, 12 to form the enclosure 10 depicts the lid member 13 having an ultrasound transducer cable clamping structure 9 for supporting the ultrasound transducer 30 within the enclosure. The cable clamping structure 9 functions to suspend and/or hold the ultrasound transducer 30 when it is positioned inside of the enclosure. The ultrasound transducer cable may be clamped by the clamping structure 9 such that the ultrasound transducer 30 is inverted inside the enclosure for disinfection. In one embodiment, as the ultrasound transducer 30 falls downwards naturally due to the effects of gravity, the whole bottom end surface of the transducer can be irradiated by the UVC LED light sufficiently.

Figure 6:
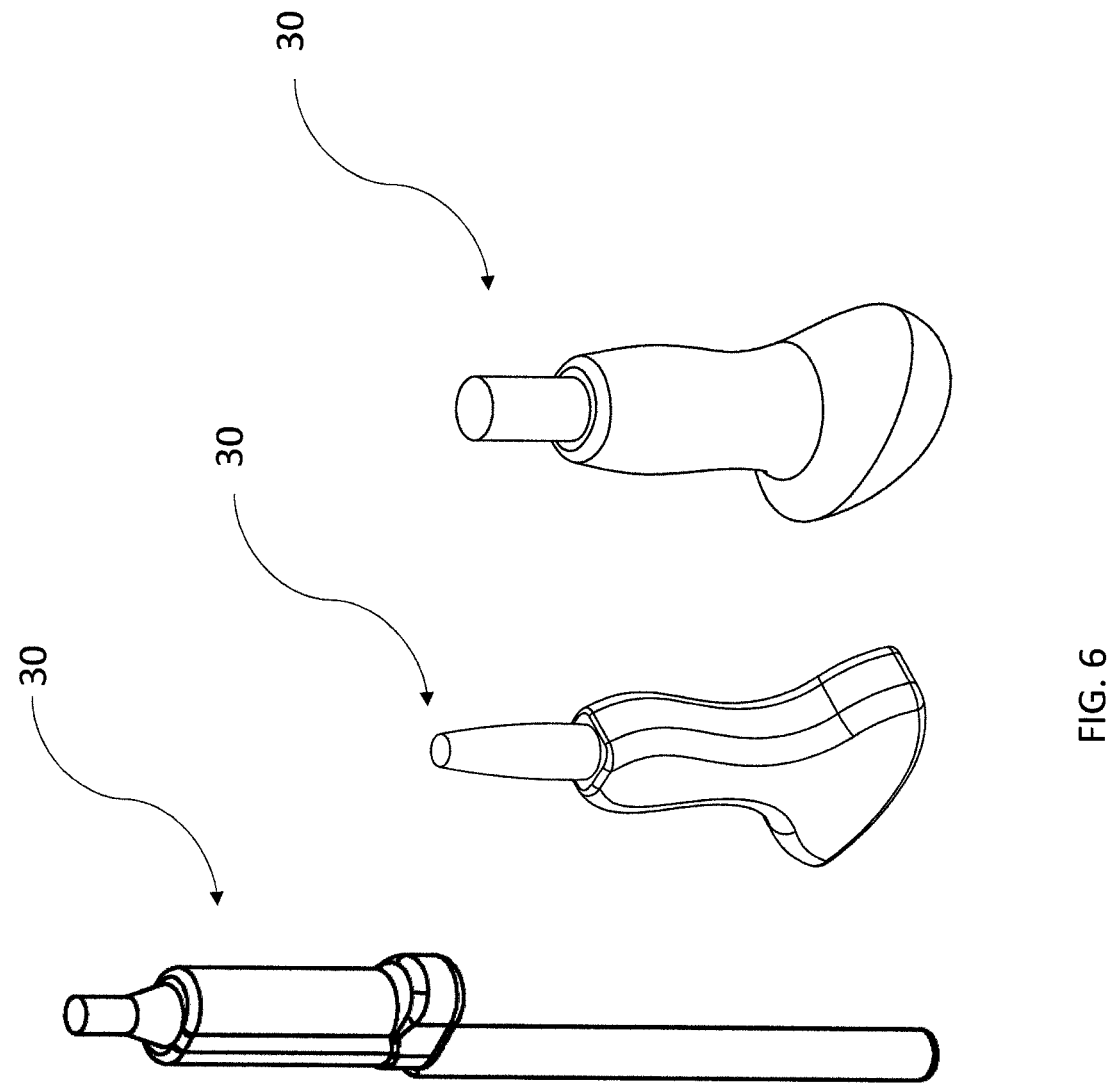
FIG. 6 depicts different kinds of ultrasound transducers suitable for use with the disinfecting device of the present invention.
Figure 7:
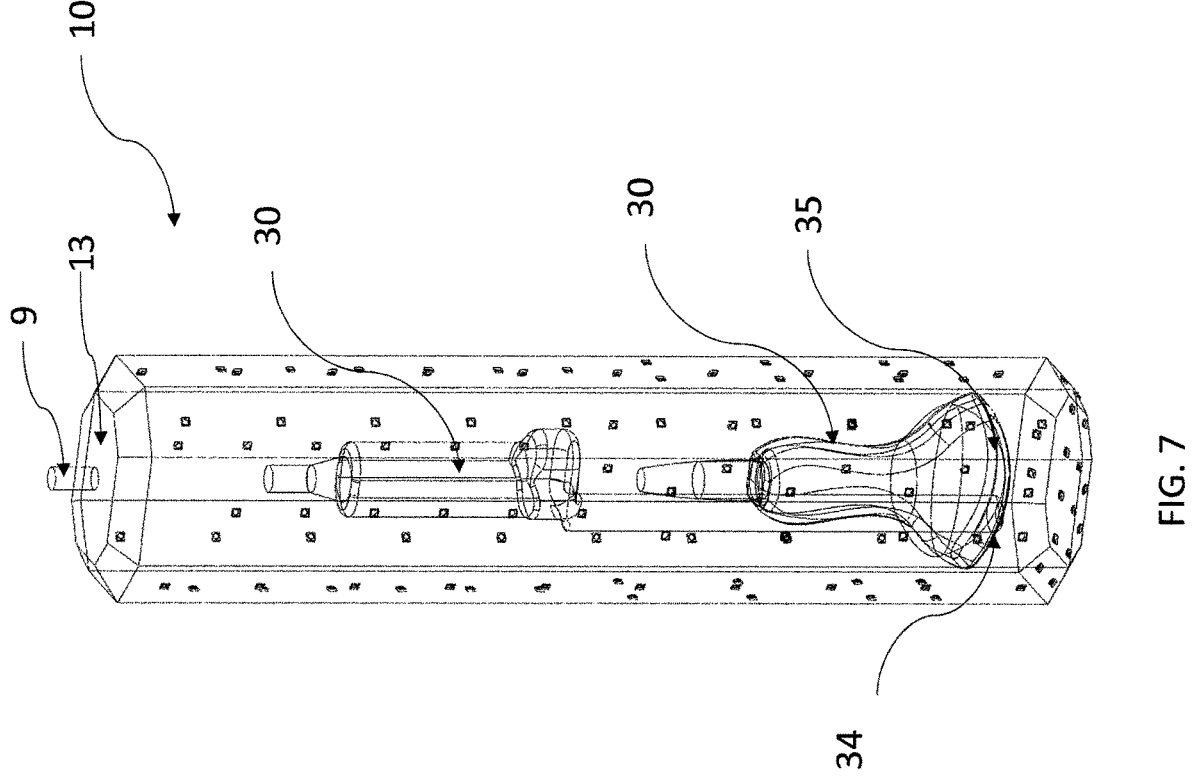
FIG. 7 shows the ultrasound transducers as described in FIG. 6 placed inside of a UVC disinfecting device in accordance with an embodiment of the present invention.

FIG. 6 depicts different types of ultrasound transducers 30 that can be used in the disinfecting enclosure of the present invention FIG. 7 shows how different ultrasound transducers 30 can be positioned inside the disinfecting enclosure 10. In this embodiment, three different types of ultrasound transducers 30 are to undergo treatment, with reference numeral 34 representing the bottom end of the upper ultrasound transducer 30 and reference numeral 35 representing the bottom end of the lower ultrasound transducer 30.

Figure 11:
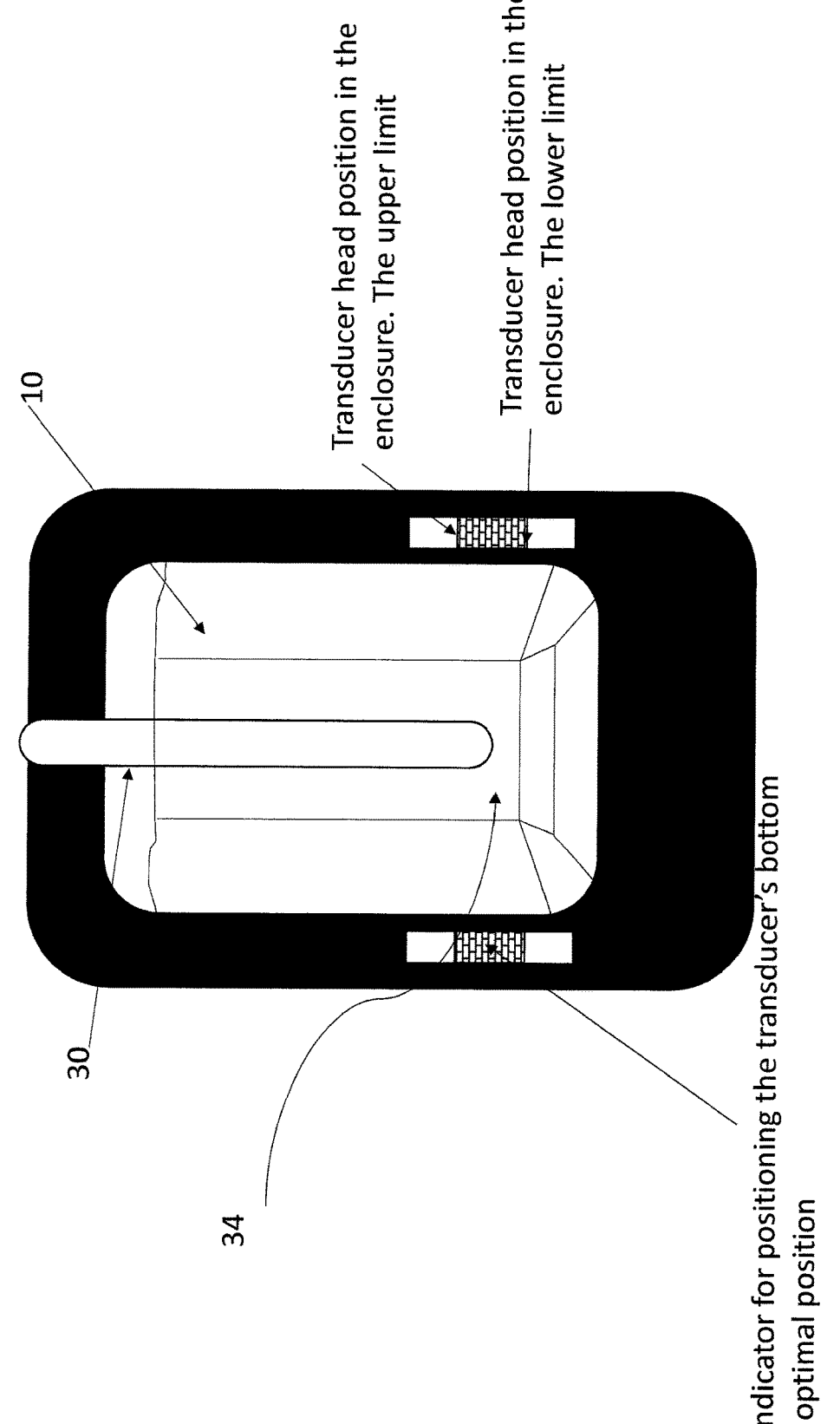
FIG. 11 shows an embodiment of a position scale marker to be located on the inside walls of the enclosure of the disinfecting device in accordance with an embodiment of the present invention.

FIG. 11 shows an embodiment of how a position scale marker may be employed within the enclosure 10 to aid an operator in positioning the transducer 30 correctly within the enclosure 10 to ensure optimal irradiation of the surface thereof. In this regard, the marker is provided to identify a preferred range of positions for the bottom end 34 of the transducer 30 to be positioned within the enclosure. Thus, when the ultrasound transducer 30 is placed within the enclosure 10, the transducer 30 is positioned in the bottom end of the enclosure 10 to be as close to the bottom of the enclosure within the limits, so that the bottom end of the transducer can be fully disinfected by the UVC LEDs positioned on the base module 12. As depicted, the range indicators may be in the form of labels adhered or otherwise applied within the side walls of the enclosure.

Figure 12:
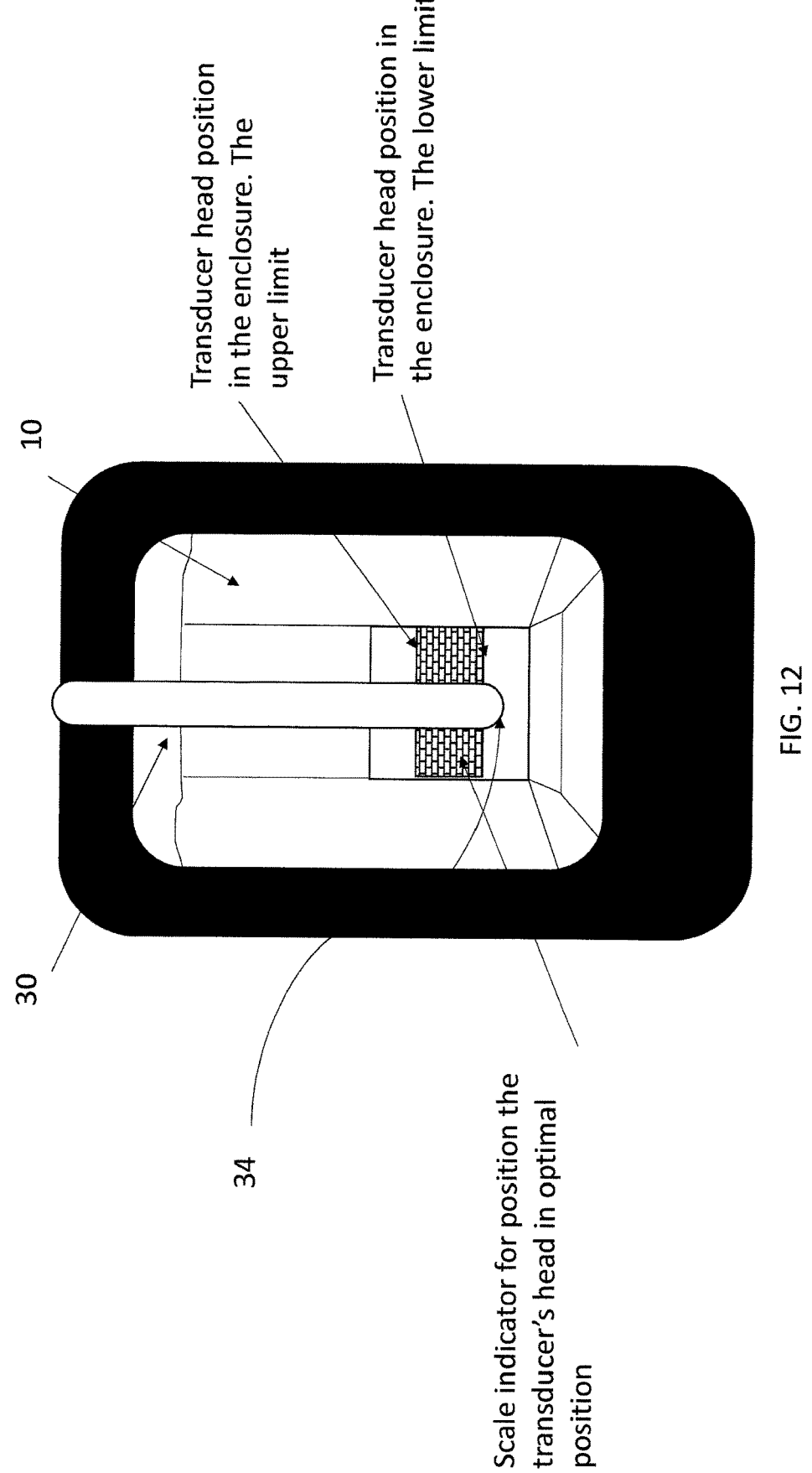
FIG. 12 shows an alternative embodiment of location indicator to be used to assist in positioning the medical instrument(s) within the enclosure of the disinfecting device in accordance with yet another embodiment of the present invention.

FIG. 12 shows another embodiment for providing a level indicator for positioning the bottom end of the transducer with respect to the bottom of the enclosure 10.

In this embodiment, the range indicators are in the form of labels adhered or otherwise applied to the inside walls of the enclosure 10.

In the embodiment of the enclosure frame assembly 20 of FIG. 3-5, recesses 25 are provided on the side members 23 and/or on the base member 21. The sidewall and the base modules 11, 12 are engaged with the recesses 25 of the side members 23 and the base member 21 such that the heatsinks 19 are connected to the light board of the modules 11, 12 so as to be disposed outside the enclosure 10. As the heat generated by the UVC LEDs is dissipated out through the heat heatsinks 19 to provide heat dissipating for the UVC LED modules.

The heatsinks 19 may further comprise heat dissipation fans (not shown) that are disposed on the rear of the sidewall modules 11 and/or the base modules 12 for heat dissipation. In an alternative arrangement, heat dissipation pipes such as condensation pipes may be disposed on the rear of the sidewall modules 11 of the enclosure for dissipating heat from the sidewall modules or base modules.

As previously discussed, in order to provide high-level disinfection, the UVC LED light source modules 11, 12 are disposed on sidewalls and bottom of the enclosure 10 respectively. The light boards 16 of each of the modules 11, 12 are disposed on the surface of the modules facing inwardly with respect to the enclosure, so that the UVC light emitted by the UVC LED 17 mounted on the light boards 16 irradiate the whole surface of the ultrasound transducer 30 mounted within the enclosure. This ensures that the whole surface of the ultrasound transducer 30 is disinfected by the UVC light, effectively avoiding any light intensity attenuation due to reflection and overheating and achieving the purpose of full and thorough high-level disinfection.

As will be appreciated, the disinfecting enclosure provided by the present invention provides an arrangement whereby the UVC LED 17 are irradiated onto the whole surface of the ultrasound transducer 30 mounted inside the enclosure. Meanwhile, heat dissipation modules are provided with each module, such that the heat generated from the UVC LEDs on the sidewall modules 11 and the base module 12 can be dissipated out of the enclosure 10 to ensure the disinfecting result inside the enclosure.

As is seen more clearly in FIG. 1 and FIG. 7, the base module 12 includes a plurality of base module pieces to cover the base of the enclosure 10, however the base module 12 may be configured such that it is a single piece comprising a flat surface. Alternatively, the base module 12 may comprise a plurality of flat and/or curved pieces. With regard to the base module 12, the light board 16 may have one or a plurality of UVC LED 17 mounted thereon to perform irradiation of the ultrasound transducer 30 located above.

As is shown in each of the depicted embodiments of the invention, in a preferred embodiment the side modules 11 are all configured to be substantially flat or planar surfaces. However, in an alternative embodiment, the sidewall modules 11 may comprise a plurality of flat or curved surfaces, each of which has one or more UVC LED 17 disposed thereon.

Figure 13:
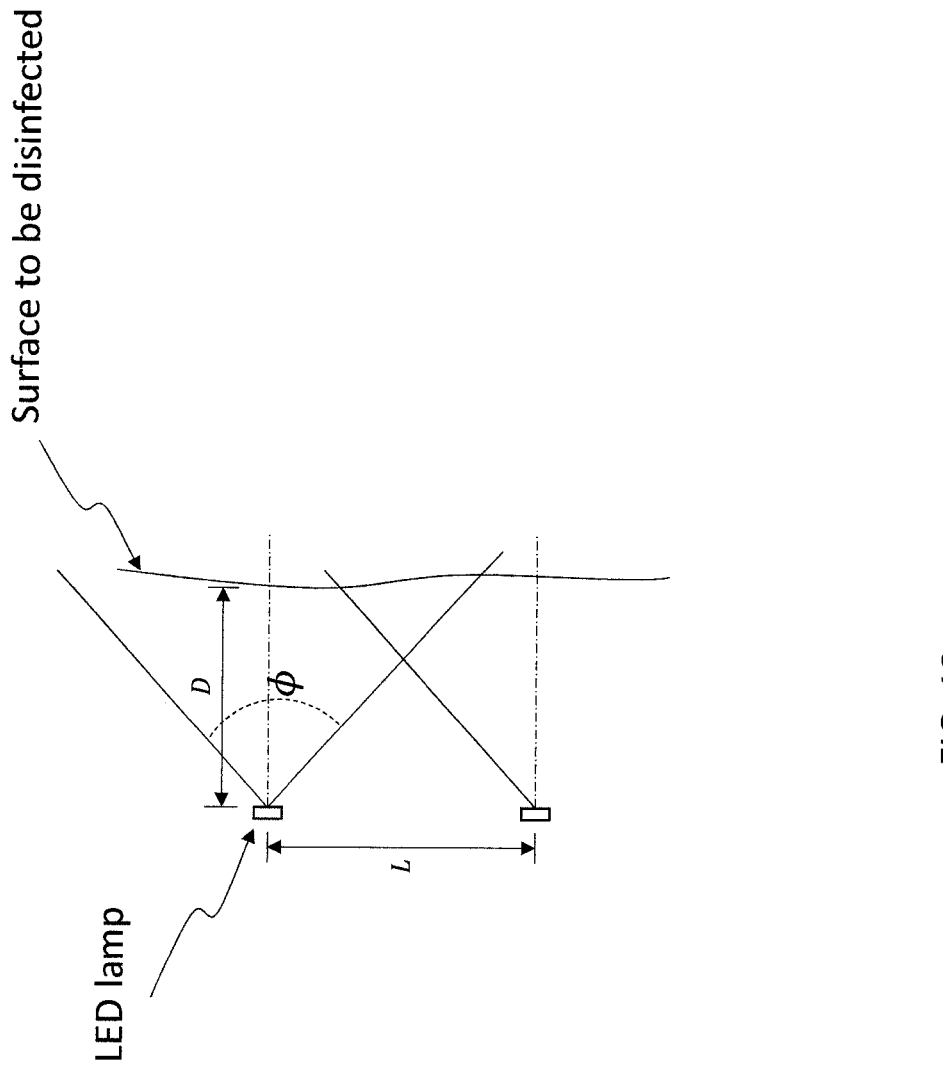
FIG. 13 shows the distance between adjacent UVC LEDs on the inner surface of the base module (denoted as "L"), the distance between the UVC LEDs and the medical instrument (denoted as "D"), and the illumination angle $\phi$ of the UVC LEDs.

Referring to FIG. 13, there is depicted a schematic diagram showing how the distance between adjacent UVC LEDs 17 on the inner surface of the base module (denoted as "L") is controlled. In this arrangement, the distance between the UVC LEDs 17 and the medical instrument 30 that is to undergo disinfection is denoted as "D", and the illumination angle of the UVC LEDs is $\phi$.

The manner in which the UVC LED 17 are arranged upon the surfaces of the light boards 16 of the side wall modules 11 and base modules 12 can be calculated to determine optimum surface irradiation of the transducers 30. The distance between the UVC LEDs on the base modules is typically less than

8

$$2D^{*\tan\frac{\phi}{2}};$$

or 15 cm

Where, D is the distance between the UVC LED 17 and the ultrasound transducer 30, and $\phi$ is the angle of illumination for the UVC LED 17.

The distance between the UVC LEDs of the sidewall light source module is typically less than:

$$2D^{*\tan\frac{\phi}{2}} \text{ Or } 15 \text{ cm};$$

Where D is the distance between the UVC LED 17 and the ultrasound transducer 30, and $\phi$ is the angle of illumination for the UVC LED 17.

Figure 8:
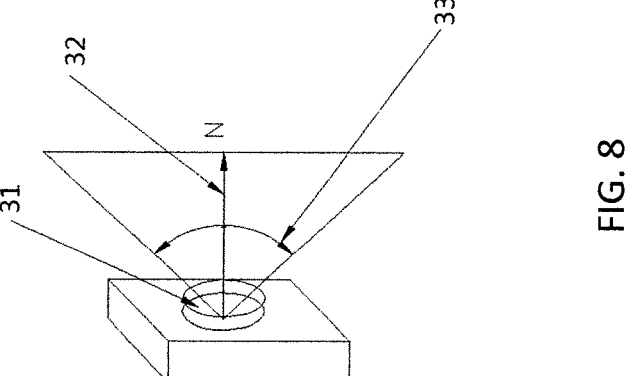
FIG. 8 is a schematic diagram showing the light emitting angle of each individual LED of the UVC LEDs of FIG. 1 in accordance with a preferred embodiment.
Figure 9:
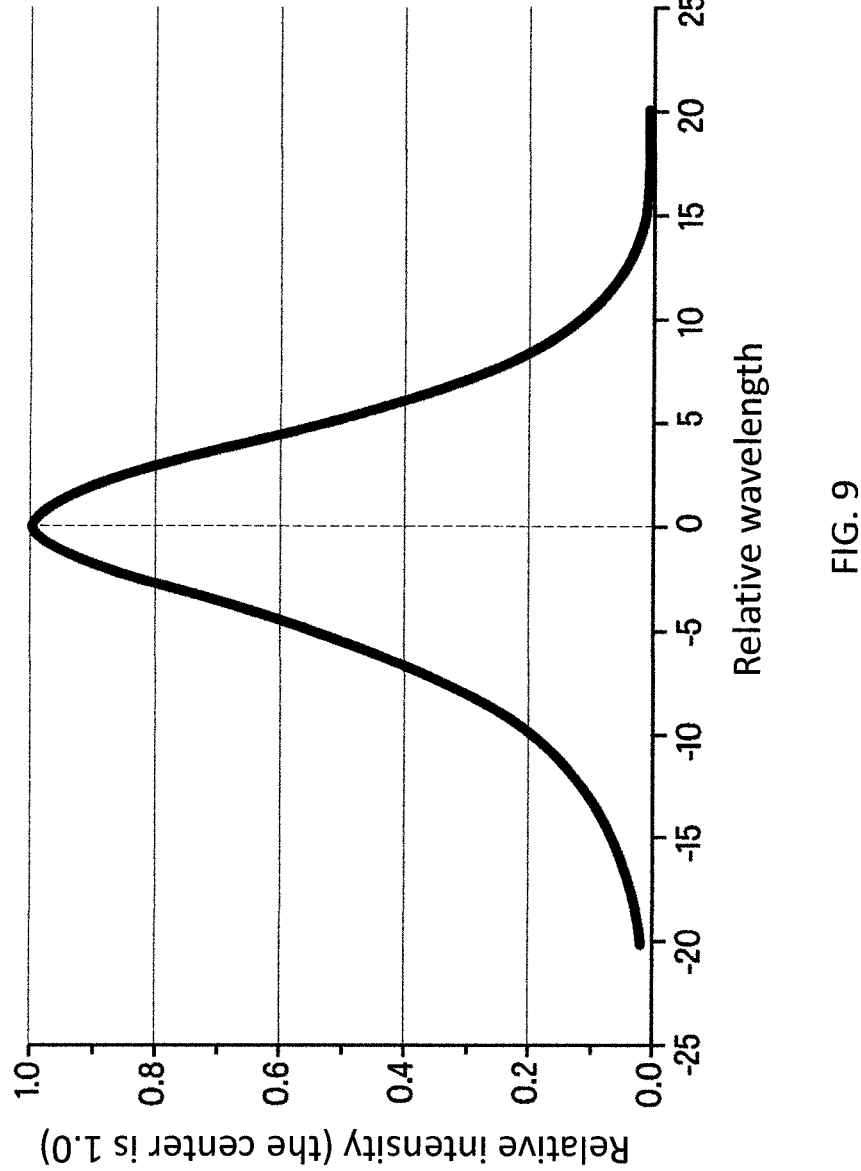
FIG. 9 shows a UVC spectrum schematic of a UVC LED in accordance with an embodiment of the present invention.

Referring to FIG. 8, a schematic diagram is provided depicting the manner in which the illumination angle of a UVC LED 17 is obtained. In this embodiment, 31 is a light emitting surface of the UVC LED 17, 32 is a normal direction of the emitting light surface, and 33 is the UVC LED emitting angle. A UVC LED spectrum schematic diagram is depicted in FIG. 9.

Figure 10:
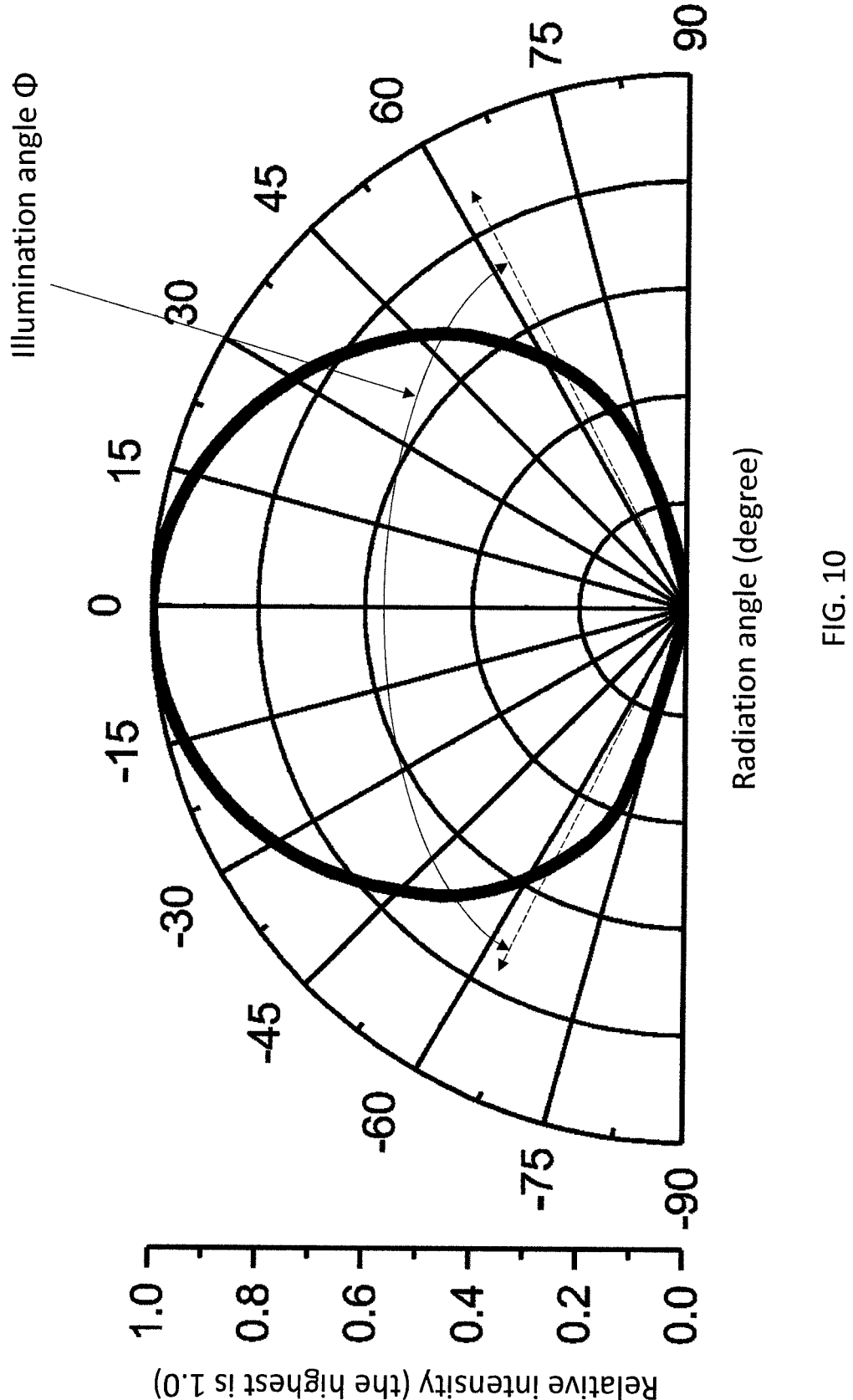
FIG. 10 shows the schematic diagram of a light distribution curve of a UVC LED in accordance with an embodiment of the present invention.

FIG. 10 is a schematic diagram providing a UVC LED lighting distribution curve, wherein the illumination angle refers to the angle when the illumination intensity of the UVC LED lighting is attenuated to 50%.

In one embodiment of the present invention, the illumination angle of the UVC LED 17 is 120°, and the distance between the UVC LED 17 and the surface of the transducer is 3 cm. In this situation, according to the present invention, the distance between adjacent UVC LED 17 on a surface of the light boards 16 of the modules 11, will be no more than 10.4 cm.

In another embodiment, if the UVC LED dispersion angle is 90°, and the distance between the light source and the transducer surface is 3 cm, the distance between adjacent UVC LED 17 on a surface of the light boards 16 of the modules 11, will be no more than 6 cm.

In general practice, the disinfecting enclosure will be configured such that the distance between the UVC LED 17 and the surface of the ultrasound transducer 30 is greater than 1 cm and less than 20 cm. If the distance described is too close, the transducer 30 may come into contact with the inner sidewall surfaces of the modules 11 when the transducer 30 is placed into the enclosure. Conversely, if the distance is too far, the irradiation on the surfaces of the transducer will be too weak to eliminate the microorganisms, resulting in disinfection times that will become too long.

Figure 14:
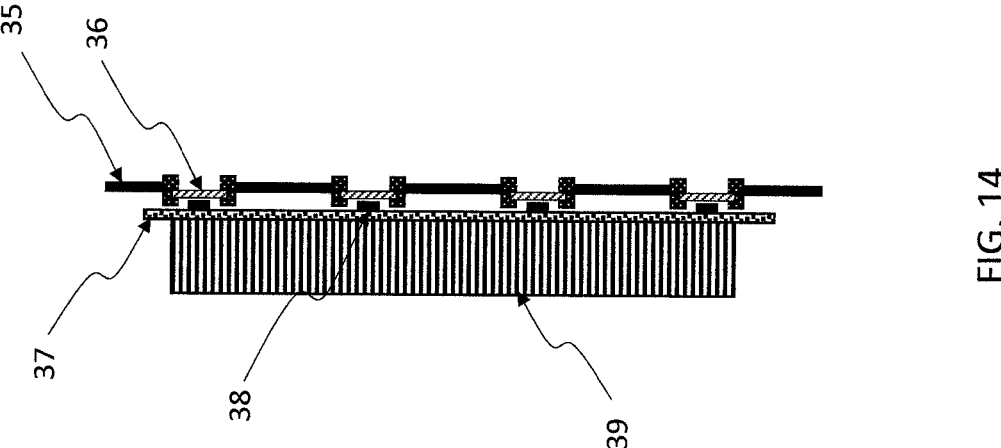
FIG. 14 is a schematic view of an alternative embodiment of a light source for use with the UVC disinfecting device in accordance with an embodiment of the present invention.

An embodiment depicting how the light source is configured, is illustrated in FIG. 14. The disinfection chamber is enclosed by one or more chamber walls 35, the chamber wall 35 comprises multiple windows 36, which are made from a material that is transparent to UVC light so as to allow the UVC light to transmit therethrough. The UVC LED chips 36 are bonded onto the light boards 37. The light boards 37 are attached to an outer side of the chamber walls, which allows the UVC LED chips 36 to face the windows 36, to transmit the UVC light through the windows 36 and into the chamber. Heat sinks 39 may be attached on the back of the light boards 37, for transmitting and dissipating heat transmission as required.

In an embodiment if the present invention, a plurality of detachable modules may be disposed about the frame of the disinfection enclosure. In another embodiment, a light source module maybe located on the detachable module, and the UVC LEDs are evenly distributed on the detachable module.

As previously discussed, each of the existing four high-level disinfecting methods for ultrasound transducers cannot achieve efficient, safe and environmentally friendly high-level disinfection. In comparing existing disinfecting methods that use UVC LEDs to form disinfecting boxes, only a small number of UVC LEDs are installed inside the disinfecting boxes, due largely to the inability of such devices to cope with the heat that is generated. As a result, such devices find it is impossible to uniformly irradiate all surfaces of the ultrasound transducer to achieve a necessary high-level disinfection. The present invention overcomes this problem and achieves a high-level disinfection by locating modules onto the sidewalls and base of a sealed enclosure. Such modules employ UVC LEDs on an inside surface thereof to achieve light irradiation on the entire surface of the ultrasound transducer. Since the enclosure is sealed, full coverage irradiation is possible, whilst substantially eliminating any UVC light leakage. Such a system ensures that the disinfecting process is efficient, safe and environmentally friendly.

It will be appreciated that with the provision of heat sinks on an outer surface of each of the modules, heat accumulation within the disinfection enclosure is significantly reduced, thereby extending the lifespan of the UVC LEDs. At the same time, it is ensured that the temperature of the disinfection enclosure is within the safe level which will not damage the transducers during the disinfecting procedure.

The above are only the preferred embodiments of the present invention and are not intended to limit the present invention. Any modifications, equivalent substitutions, and improvements made within the spirit and principles of the present invention should be included in the range of protection of the present invention.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

Orientational terms used in the specification and claims such as vertical, horizontal, top, bottom, upper and lower are to be interpreted as relational and are based on the premise that the component, item, article, apparatus, device or instrument will usually be considered in a particular orientation, typically with the enclosure uppermost.

It will be appreciated by those skilled in the art that many modifications and variations may be made to the methods of the invention described herein without departing from the spirit and scope of the invention.

The claims defining the invention are as follows:

1. A disinfecting enclosure for a medical instrument comprising:
a plurality of modules arranged in an abutting configuration to define an enclosure having a base and at least one upright wall extending from the base; and
a lid member configured to be mounted on the at least one upright wall so as to enclose the enclosure, the lid member having a clamping mechanism for locating the medical instrument inside of the enclosure such that the medical instrument is consistently positioned within the enclosure for disinfection;
wherein each said module comprises a frame member configured to receive a board having a plurality of UVC LEDs mounted upon a surface thereof, each of the plurality of UVC LEDs are configured to emit UVC light to irradiate surfaces of the medical instrument located within the enclosure, and a heat dissipation member mounted to a rear surface of the board to be in direct contact with the board to dissipate heat generated by each UVC LED away from the enclosure, the frame member functions to form a perimeter of the module and to retain the heat dissipation member in direct contact with the board.

2. A disinfecting enclosure according to claim 1, wherein the distance between adjacent UVC LEDs mounted on the board of a surface of the module positioned to form the base of the enclosure is less than:

$$2D^{*\tan\frac{\phi}{2}} \text{ or } 15 \text{ cm};$$

where, D is the distance between the UVC LEDs and the medical instrument and $\phi$ is an illumination angle of the UVC LEDs.

3. A disinfecting enclosure according to claim 1, wherein the distance between adjacent UVC LEDs mounted on the surface of the board of the module positioned to form the at least one upright wall of the enclosure is less than:

$$2D^{*\tan\frac{\phi}{2}} \text{ or } 15 \text{ cm};$$

where D is the distance between the UVC LEDs and the medical instrument and $\phi$ is an illumination angle of the UVC LEDs.

4. A disinfecting enclosure according to claim 1, wherein each of the plurality of modules further comprises a plurality of side wall modules are arranged in an abutting configuration to form the at least one upright wall of the enclosure and at least one base module for forming the base of the enclosure.

5. A disinfecting enclosure according to claim 4, wherein a plurality of base modules are arranged in an abutting configuration to form the base of the enclosure.

6. A disinfecting enclosure according to claim 5, wherein the plurality of base modules have a flat and/or curved configuration to form the base of the enclosure.

7. A disinfecting enclosure according to claim 4, wherein the at least one base module comprises a single module having a flat surface.

8. A disinfecting enclosure according to claim 4, wherein the at least one base module has a plurality of UVC LED mounted on the board thereof to perform irradiation of the medical instrument located within the enclosure.

9. A disinfecting enclosure according to claim 4, wherein the side wall modules are configured to be substantially flat or planar surfaces.

10. A disinfecting enclosure according to claim 1, further comprising a frame having a plurality of open spaces into which the plurality of modules is inserted to form the enclosure.

11. A disinfecting enclosure according to claim 10, wherein the enclosure is in the form of a polyhedron and the modules are arranged in an abutting configuration to form a base and sidewalls of the polyhedron.

12. A disinfecting enclosure according to claim 11, wherein the polyhedron is an octagonal polyhedron.

13. A disinfecting enclosure according to claim 1, wherein the heat dissipation member comprises a heat sink mounted on an external surface of each of the modules that conducts heat from the UVC LEDs to the outside of the enclosure.

14. A disinfecting enclosure according to claim 1, wherein a distance between the UVC LEDs and the medical instrument when the medical instrument is located within the enclosure is greater than 1 cm and less than 20 cm.

15. A disinfecting enclosure according to claim 1, wherein an internal surface of the enclosure has one or more indicators to assist in positioning the medical instrument with respect to the base of the enclosure.

16. A disinfecting enclosure according to claim 1, wherein the medical instrument is an ultrasound transducer.

\* \* \* \* \*